United States Patent [19]
Freitas

[11] Patent Number: 5,125,910
[45] Date of Patent: Jun. 30, 1992

[54] SURGICAL ENDOSCOPIC SUCTION/IRRIGATION CANNULA ASSEMBLY

[75] Inventor: Michael W. Freitas, San Jacinto, Tex.

[73] Assignee: Dexide, Inc., Fort Worth, Tex.

[21] Appl. No.: 656,951

[22] Filed: Feb. 19, 1991

[51] Int. Cl.$^5$ ............................................. A61M 5/00
[52] U.S. Cl. ................................. 604/249; 604/246; 604/264; 128/4
[58] Field of Search ............... 604/173, 246, 249, 169, 604/167, 164, 158, 264, 902; 128/4

[56] References Cited

U.S. PATENT DOCUMENTS

| | | | |
|---|---|---|---|
| 4,341,224 | 7/1982 | Stevens | 128/675 |
| 4,447,236 | 5/1984 | Quinn | 604/169 |
| 4,655,752 | 4/1987 | Honkanen et al. | 604/167 X |
| 4,696,305 | 9/1987 | von Berg | 604/249 X |

Primary Examiner—John J. Wilson
Assistant Examiner—Jeffrey A. Smith
Attorney, Agent, or Firm—Jackson & Walker

[57] ABSTRACT

The invention relates to a surgical endoscopic suction-/irrigation cannula assembly and, in particular, to a valve actuator for selectively transmitting liquid or gas into or out of a suction/irrigation cannula. The valve actuator includes a manually operated elastomeric valve head. The actuator may contain a port disposed therethrough and in alignment with a cannula tubing for introduction of an endoscopic or laparoseopic surgical instrument while the assembly including the valve actuator is positioned within a body cavity during surgery.

3 Claims, 2 Drawing Sheets

SURGICAL ENDOSCOPIC SUCTION/IRRIGATION CANNULA ASSEMBLY

BACKGROUND OF THE INVENTION

(1) FIELD OF THE INVENTION

The invention relates to a surgical endoscopic suction/irrigation cannula assembly including a valve actuator.

(2) DESCRIPTION OF THE PRIOR ART

Surgical endoscopic procedures typically follow three steps. First, a cannula, such as a Veress cannula, is inserted into the abdominal cavity through in the abdominal wall and the cavity is inflated with insufflating gas which is passed through the cannula tubular housing. After insufflating, a small incision is made in the skin and a standard trocar spike is thrust into the inflated abdomen through the bore of the trocar tube. The spike is inserted for purposes of puncturing or cutting of the abdominal wall and piercing the fascio and peritoneum inside the cavity. After removal of the spike, a suction/irrigation cannula is inserted through the trocar housing and into the opening so that fluids may be drained from the body cavity.

Endoscopic surgery also includes the introduction through a trocar tube of a number of auxiliary surgical instruments such as, for example, a laparoseope, or the like. Heretofore, in many surgical instances, endoscopic surgery procedures have been performed through the trocar tubular housing by sequential insertion and removal of surgical instruments as they are needed. As the surgery is performed using such instruments, many situations require concurrent introduction or removal of gaseous or liquid fluid materials immediate the area of the surgery. Thus, removal of a surgical instrument from the body cavity through the trocar tubular housing and reinsertion through the trocar housing of a device for transmission of the gaseous or liquid substance not only complicates the surgical procedure, but is also time consuming and may introduce unforseeable consequences to the surgical operation.

Endoscopic surgery is a very fine art, demanding extremely controlled movements of the surgeon's hand in the operation of the surgical instruments through the trocar housing. Therefore, any valves which are required to be manipulated by the surgeon must be extremely sensitive and manipulatable in direct response to a very minor application of pressure or movement of the surgeon's hand or finger.

The present invention addresses the problems set forth above. In particular, the present invention provides a combination surgical endoscopic suction/irrigation cannula assembly which includes a valve actuator. The invention permits the introduction or removal of fluid to or from the body cavity during surgery by activation with only a minor amount of pressure through the surgeon's finger and provides a positive comparatively frictionless repeatable valve head and seat assembly. In addition, the present invention provides a means for introducing or removing fluid from the body cavity during surgery through the cannula housing through which an auxiliary device may be inserted at any time during the surgery without removal of the valve actuator device, thus permitting the auxiliary endoscopic instrument to be utilized concurrently with a device which will also permit introduction of and/or removal of gaseous or liquid fluids from the body cavity during the surgical operation.

SUMMARY OF THE INVENTION

The present invention provides a surgical endoscopic cannula assembly. The assembly comprises and elongate tubular housing having a first open end for introduction into a body cavity and a second open end. A valve actuator assembly is carried on the tubular housing and is in fluid communication with the tubular housing through the second open end. The valve actuator assembly includes an actuator housing. At least one valve chamber is provided within the actuator housing. An elastomeric normally retracted selectively expansible valve head member is disposed in the chamber, together with a valve seat which normally sealingly receives the valve head and which is defined on the actuator housing. A manually operable valve head controller is carried on the actuator housing for elastically expanding the valve head in a direction to move the valve head away from sealing receipt relative to said valve seat. A fluid passageway includes the chamber and extends within the actuator housing and through the elongate tubular housing of the cannula. A port is disposed through the actuator housing and is in fluid communication with the chamber for receiving a fluid transmitting means for urging fluid into or out of the tubular housing and through the chamber.

DESCRIPTION OF THE PREFERRED EMBODIMENTS

Figure 1:
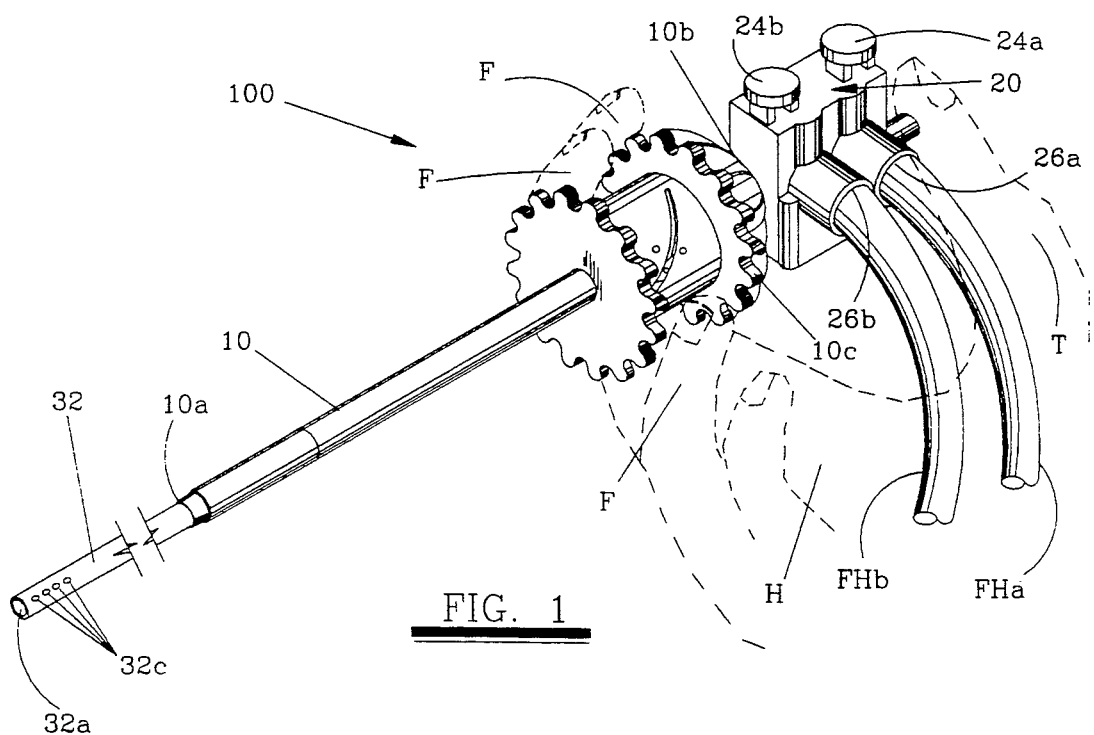
FIG. 1 is an isometric view of the surgical endoscopic cannula assembly introduced through a trocar housing and held in the hands of a surgical operator.

Now, with first reference to FIG. 1, there is shown the surgical endoscopic cannula assembly 100 of the present invention disposed through an elongate tubular cannula housing 10 and held in such position prior to use during surgery and introduction through a body cavity by means of application of a surgeon's fingers F holding a finger grasp 10c while the surgeon's thumb T grasps the end of a valve actuator assembly 20.

An elongate tubular housing 32 of the actuator assembly 20 is shown inserted through the inboard-most end 10b of the assembly 20 and extending through the outboard-most open end 10a of the cannula housing 10, with the elongate tubular housing 32 having a first open end 32a with transverse ports 32c immediate the open end 32a.

As shown, plural fluid hoses FHa, FHb are secured to the valve actuator assembly 20 through respective ports 26a, 26b, with the hoses FHa, FHb, extending to a body of pressured fluid for introduction through the actuator assembly 20 and the housing 32 and into the body cavity during surgery, and/or, to a vacuum generating means for removal of fluid, by suction, through the open end 32a, thence through the housing 32 and into the actuator assembly 20, during the surgical operation.

Figure 2:
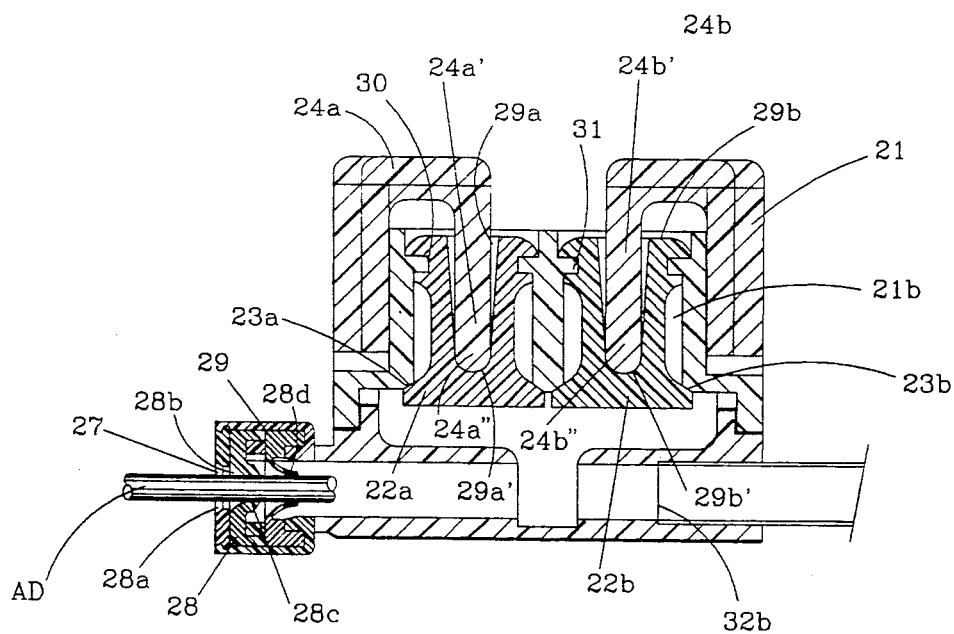
FIG. 2 is a partial sectional view through the valve actuator assembly with the valve members therein being in closed position.

Now referring to FIG. 2, there is shown the valve actuator assembly 20 of the present invention with plural valve assemblies therein. The actuator assembly is defined by an exterior actuator housing 21 having a lower body member 21a for sealing receipt of the second open end 32b of the elongate tubular housing 32.

Within the housing are first and second elastomeric valve heads 22a, 22b which are shown, as in FIG. 2, sealingly engaged upon respective valve seats 23a, 23b circularly defined around the innermost portion of the actuator housing 21 and contourly profiled for companion sealing receipt of the valve head member 22a, 22b.

The valve heads 22a, 22b, are selectively expansible elastomeric elements which have an elasticized "memory", such that cyclic expansion of the heads 22a, 22b, away from the respective seat 23a, 23b, does not adversely effect the ability of the heads 22a, 22b, to contourly retract for sealing engagement on the respective seat 23a, 23b. Preferably, the valve heads are composed of silicon rubber or a neoprene or natural rubber.

Each of the valve heads 22a, 22b has a centrally defined upwardly open valve head cavity 29a, 29b for receipt therein of a protruding finger 24a', 24b' having a fingertip 24a", 24b" contourly shaped for mating contact with an upwardly facing shaped cavity end 29a', 29b' of the valve head 22a, 22b.

Each of the fingers 24a', 24b' extend from and are a part of a valve head controller 24a, 24b which is manipulated by a thumb T or finger F of the surgeon's hand H by slight downward touch application during surgery, as described more fully hereafter.

The valve heads 22a, 22b, are held in normally closed position relative to the housing 21 and the valve seat 23a, 23b, by means of a circumferentially extending contoured rib element 31 received within a companion circumferential groove 30 defined around the uppermost end portion of the respective valve head 22a, 22b.

A valve chamber 21a, 21b, is defined exteriorly around the elastomeric valve head member 22a, 22b, and interior of the actuator housing 21 and is always in communication through the respective port 26a, 26b, with the fluid hose FHa, FHb.

Figure 3:
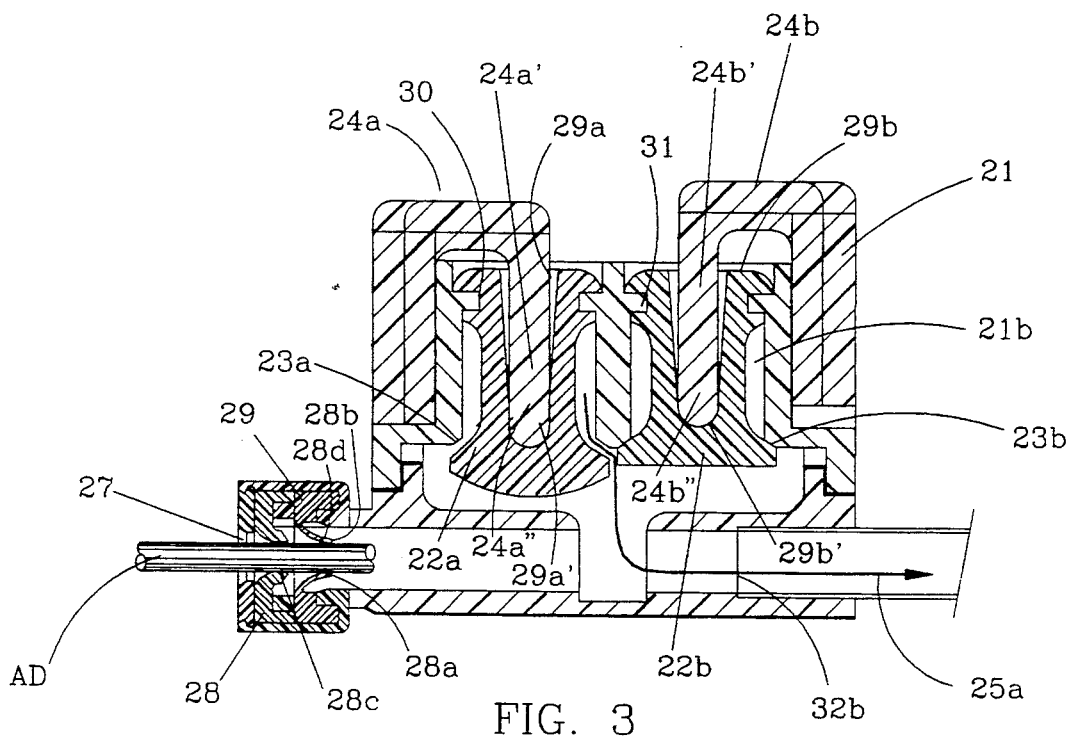
FIG. 3 is a view similar to that of FIG. 2 showing one of the valve members in the actuator being opened for passage of fluid therethrough.
Figure 4:
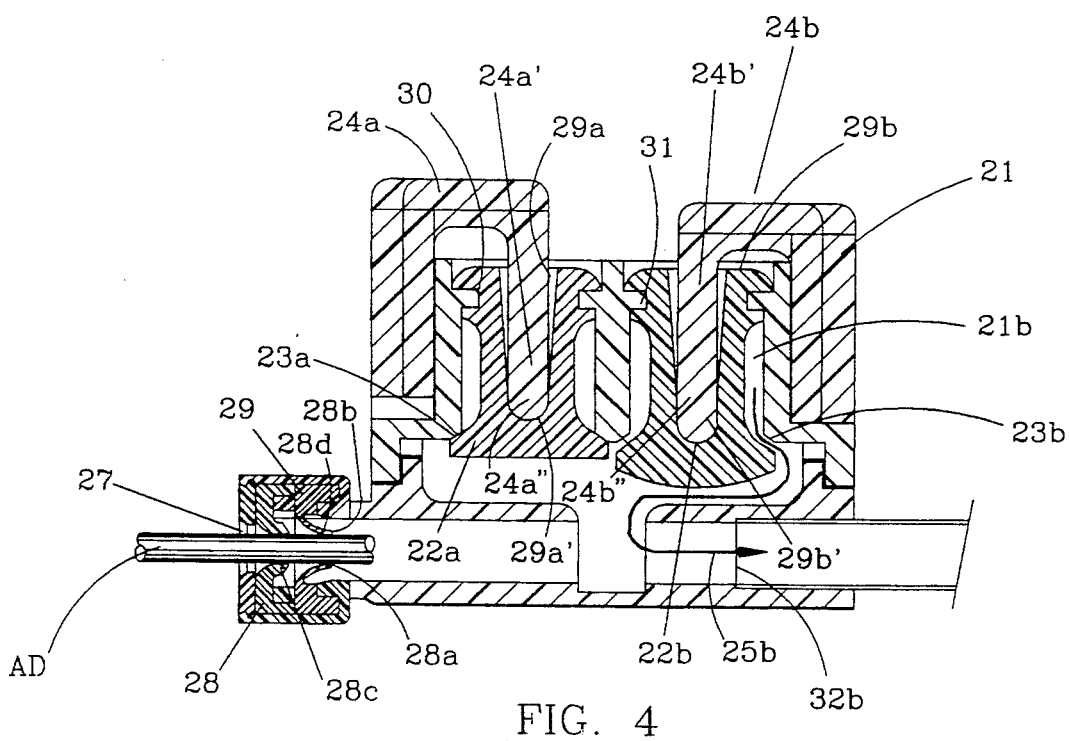
FIG. 4 is a view similar to that of FIGS. 2 and 3, showing the other of the valve members in the actuator being opened and the first valve member being closed for transmission of another fluid therethrough.

A fluid passageway 25a (FIG. 3) and 25b (FIG. 4) is defined through the actuator assembly 20 and includes the valve chamber 21a when the valve seat 23a is sealingly away from the valve head 22a (FIG. 3) likewise, the fluid passageway 25b extends from the fluid hose FHb by means of the port 26b through the chamber 21b when the valve head 22b is sealingly away from its valve seat 23b (FIG. 4). These fluid passageways 25a, 25b, may carry fluid in the form of a liquid in one or both of the fluid hoses FHa, FHB, for introduction into the actuator assembly 20 and the tubular cannula housing 10, and discharged through the open end 32a and the transverse ports 32c into the body cavity during surgery. Alternatively, one or both of the fluid passageways 25a, 25b, may provide a fluid vacuum passage extending to one or both of the fluid hoses FHa, FHb, for removal of fluid from the body cavity during surgery.

The actuator housing 21 also has a selectively openable port 27 opposite the opening 21a for introduction of an auxiliary device AD, such as a laparoscope, which may be concurrently utilized during the surgery in combination with the actuator assembly 20. As will be appreciated from the disclosure herein, and particularly with respect to FIGS. 1 and 2, the auxiliary device AD may be introduced through the valve actuator assembly 20 and the elongate tubular cannula housing 10 and the tubular housing 32 of the assembly 100 while concurrently manipulating one or both of the valve head controllers 24a, 24b, to introduce or remove fluid during surgery.

The port 27 is always sealingly closed by means of a seal assembly comprising a first seal 28 and a second seal means 29. The first seal 28 has a concave curvature, such as 28a, and incorporates a lateral slit 28b to accomodate entrance of the auxiliary device AD therethrough. When the auxiliary device AD is introduced through the assembly 20, as shown in FIGS. 2, 3 and 4, first and second seal lips 28c, 28d will seal around the exterior of the auxiliary device AD to prevent passage of fluid and pressure thereacross from the interior of the assembly 20, to the exterior thereof, through the port 27. Additionally, when the auxiliary device AD is not within the assembly 20, the second seal means 29, prevents fluid from passing from the exterior to the interior, and vice versa.

OPERATION

When it is desired to perform endoscopic surgery, the cannula housing 10 is introduced through the body cavity and held by the surgeon as shown in FIG. 1. The valve actuator assembly 20 may be introduced into the cannula housing 10 prior to introduction of the housing 10 into the body cavity, or concurrently therewith.

When it is desired to introduce or remove fluid to or from the body cavity, one or more of the valve head controllers 24a, 24b, are manipulated to move the respective valve head 22a, 22b, from sealing engagement with the respective valve seat 23a, 23b, by causing the valve head 22a, 22b, to become selectively elastomerically expanded. By slight application of downward pressure through the surgeon's finger F touching the valve head controller 24a, 24b, a smooth, substantially frictionless movement of the head 22a, 22b, from the seat 23a, 23b, will occur, such that the valve chamber 21a, 21b, forms a part of the fluid passageway 25a, 25b. When it is desired to terminate the introduction or withdrawal of fluid, as above described, the surgeon's finger F, or thumb T, is removed from the valve head controller 24a, 24b. Now, the stored energy defined by the application of the controller 24a, 24b to the elastomeric valve head 22a, 22b, during the opening operation, as above described, permits the head 22a, 22b, to be deenergized, such that the elastomeric "memory" of the head 22a, 22b, permits the head 22a, 22b, to be retracted to the seating engagement with the respective valve seal seat 23a, 23b, and the respective chamber 21a, 21b, is sealingly isolated from the remaining portion of the fluid passageway 25a, 25b.

Although the invention has been described in terms of specified embodiments which are set forth in detail, it should be understood that this is by illustration only and that the invention is not necessarily limited thereto, since alternative embodiments and operating techniques will become apparent to those skilled in the art in view of the disclosure. Accordingly, modifications are contemplated which can be made without departing from the spirit of the described invention.

What is claimed and desired to be secured by Letters Patent is:

1. A surgical endoscopic cannula assembly, comprising: an elongate tubular housing means having a first open end for introduction into a body cavity, and a second open end; a valve actuator assembly carried on said tubular housing means and in fluid communication with said tubular housing means through said second open end said valve actuator assembly including an actuator housing; first and second valve chambers within said housing; an elastomeric normally retracted selectively expansible valve head member disposed in each of said valve chambers; a valve seat in each said chamber normally sealingly receiving a respective valve head and defined on said housing; a manually operable valve head controller for each said valve head and carried on said housing for elastically expanding the respective valve head in a direction to move the respective valve head away from sealing receipt relative to the respective valve seat; first and second fluid passageways including said chambers and extending within said tubular housing means and through said tubular housing means, one of said passageways being intercepted by one of said valve head and valve seats and the other of said fluid passageways being intercepted by the other of said valve head and valve seats, one of said fluid passageways providing means for transmission of a liquid therethrough and the other of said fluid passageways providing means for transmission of a gaseous vacuum therethrough; and first and second ports disposed through said housing and in respective fluid communication with said first and second chambers for receiving a fluid transmitting means for urging fluid into or out of said tubular housing through said respective chambers.

2. A combination surgical endoscopic cannula and trocar assembly, comprising: an elongate trocar cannula tubular housing means having a first open end portion for positioning through a body wall during surgery and a second opposite end portion for introduction and removal of a cannula therethrough while said first open end portion is positioned through the body wall; an elongate cannula tubular housing means having a first open end for introduction into the body cavity and a second open end; a valve actuator assembly carried on said cannula tubular housing means and in fluid communication with said cannula tubular housing means through said second open end said valve actuator assembly including an actuator housing; first and second valve chambers within said actuator housing; an elastomeric normally retracted selectively expansible valve head member disposed in each of said valve chambers; a valve seat in each said chamber normally sealingly receiving a respective valve head and defined on said actuator housing; a manually operable valve head controller for each said valve head and carried on said actuator housing for elastically expanding the respective valve head in a direction to move the respective valve head away from sealing receipt relative to the respective valve seat; first and second fluid passageways including said chamber and extending within said tubular housing and through said .tubular housing, one of said passageways being intercepted by one of said valve head and valve seats and the other of said fluid passageways being intercepted by the other of said valve head and valve seats, one of said fluid passageways providing means for transmission of a liquid therethrough and the other of said fluid passageways providing means for transmission of a gaseous vacuum therethrough; and first and second ports disposed through said housing and in respective fluid communication with said first and second chambers for receiving a fluid transmitting means for urging fluid into or out of said tubular housing through said respective chambers 3. The assembly of claim 1 or claim 2 further including: a groove and rib configuration defined between each of said valve heads and said actuator housing for securing each of said valve heads within said respective chamber and for resisting elastic expansion of each of said valve heads in the direction to move said valve heads away from said valve seats.

* * * * *